(12) United States Patent
Jaynes

(10) Patent No.: US 9,400,933 B2
(45) Date of Patent: Jul. 26, 2016

(54) METHOD, APPARATUS, AND COMPUTER PROGRAM PRODUCT FOR THE IDENTIFICATION AND PACKAGING OF MEDICATION

(71) Applicant: Aesynt Incorporated, Cranberry, PA (US)

(72) Inventor: Robert Jaynes, Pittsburgh, PA (US)

(73) Assignee: Aesynt Incorporated, Cranberry, PA (US)

( * ) Notice: Subject to any disclaimer, the term of this patent is extended or adjusted under 35 U.S.C. 154(b) by 266 days.

(21) Appl. No.: 14/104,518

(22) Filed: Dec. 12, 2013

(65) Prior Publication Data

US 2015/0169829 A1    Jun. 18, 2015

(51) Int. Cl.
  *G06K 9/00* (2006.01)
  *G06K 9/18* (2006.01)
  *G06F 19/00* (2011.01)

(52) U.S. Cl.
  CPC .............. *G06K 9/18* (2013.01); *G06F 19/3456* (2013.01); *G06K 9/00* (2013.01)

(58) Field of Classification Search
  CPC ............................. G06F 19/3456; G06K 9/18
  See application file for complete search history.

(56) References Cited

U.S. PATENT DOCUMENTS

| | | | |
|---|---|---|---|
| 7,930,064 B2* | 4/2011 | Popovich, Jr. ...... | G07F 17/0092 221/2 |
| 8,738,177 B2* | 5/2014 | van Ooyen .............. | B65C 1/026 700/235 |
| 9,150,119 B2* | 10/2015 | Henderson ............. | B60M 1/305 |
| 2002/0065728 A1* | 5/2002 | Ogasawara .......... | G06Q 20/208 705/23 |
| 2014/0039672 A1* | 2/2014 | Niinisto ............... | G06F 19/3462 700/240 |
| 2014/0122889 A1* | 5/2014 | Freund .................... | G01S 19/14 713/176 |
| 2015/0066205 A1* | 3/2015 | Braun ................. | G06F 19/3462 700/235 |
| 2015/0169829 A1* | 6/2015 | Jaynes ................ | G06F 19/3456 705/3 |

* cited by examiner

*Primary Examiner* — Gregory M Desire
(74) *Attorney, Agent, or Firm* — Alston & Bird LLP

(57) ABSTRACT

Provided herein are a method and apparatus for identifying and labeling medications in overpack containers, and more specifically, to identifying a medication and generating information relating to the medication to be included on a label for an overpack container of the medication. In particular, methods may include receiving an article at an imaging station, capturing images of the article from a plurality of positions about the imaging station, receiving the article into a container, and identifying the article from at least one of the captured images. The at least one of the captured images may include identifying indicia. Methods may also include generating information related to the identified article in response to identifying the article, and causing the information related to the identified article to be presented on a label associated with the container. Generating information related to the identified article may include generating destination information associated with the article.

19 Claims, 7 Drawing Sheets

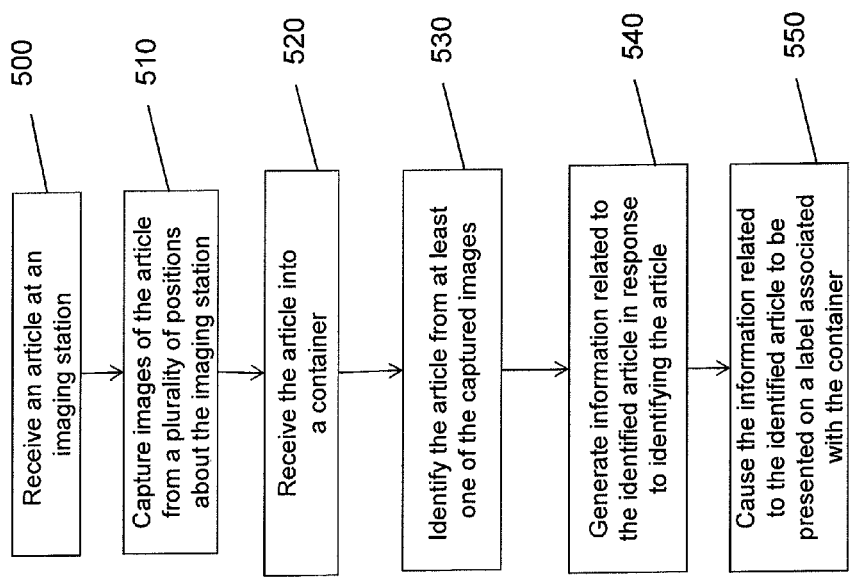

METHOD, APPARATUS, AND COMPUTER PROGRAM PRODUCT FOR THE IDENTIFICATION AND PACKAGING OF MEDICATION

FIELD OF THE INVENTION

The present invention relates to the identification of articles in a packaging system, and more particularly to providing a method, apparatus, and computer program product for ensuring accuracy and efficiency of the identification of medications packaged in a pharmaceutical dispensing system.

BACKGROUND

Medications are an important part of an effective healthcare system and it is important that medications are properly prescribed, distributed, and consumed. Advances in medication development have led to a proliferation of available medications for virtually any health condition. The vast number of medications available for patients can require pharmacies and hospitals to maintain very large inventories of medications with hundreds of types available at any given time. The large number of medications available may increase the likelihood of distributing the incorrect medication type or dosage to a patient. Manual verification of medicines, including the type and dosage, is generally required to minimize errors in distribution. However, as the number of available medications increases, the number of medications distributed to patients similarly increases. This increase has led to the automation of various steps of the medication distribution process.

Automated dispensing and packaging of medications is a process which must be executed with great accuracy to ensure patient safety and to minimize possible errors. Due to various phases of the distribution process, from the manufacturer to the wholesale distributor to the pharmacy to the patient, automation can be implemented in one or all of the distribution phases. However, upstream errors in packaging can be problematic if not caught before dispensing to a patient. Therefore, manual verification is still generally required to ensure accuracy of medication identification before it is distributed to a patient.

SUMMARY

Provided herein is an invention to improve the accuracy and efficiency of automated medication identification, packaging, and distribution. According to some embodiments, medications may be efficiently and accurately repackaged into overpack containers without requiring 100% pharmacist verification. Further, repackaging of the medication may be expedited and conducted without regard to a particular order as medications and supplies can be accurately identified at the repackaging step in order to properly label an overpack receiving the medication or supply according to what is received therein.

Example embodiments of the present invention may provide an efficient method of identifying and labeling medications in overpack containers, and more specifically, to identifying a medication and generating information relating to the medication to be included on a label for an overpack container of the medication. In particular, methods may include receiving an article at an imaging station, capturing images of the article from a plurality of positions about the imaging station, and identifying the article from at least one of the captured images. The at least one of the captured images may include identifying indicia. Methods may also include generating information related to the identified article in response to identifying the article, and causing the information related to the identified article to be presented on a label associated with a container into which the article is received. Generating information related to the identified article may include generating destination information associated with the article. The identifying indicia may include a barcode. The container may include a bin and causing information related to the identified article to be presented on a label associated with the container may include causing an electronic display to present the information related to the identified article.

Methods of example embodiments may also include generating and storing to a memory a record including the at least one of the captured images and the information related to the identified article. Methods may optionally include providing for presentation of the record to a user and receiving verification that the at least one of the captured images and the information related to the identified article are correct. The imaging station may include a plurality of image capture devices disposed about a receiving area, and receiving an article at the imaging station may include receiving an article through the receiving area at an uninterrupted pace. Capturing images of the article from a plurality of positions about the imaging station may include capturing images of the article as the article moves through the receiving area at an uninterrupted pace. The uninterrupted pace may be a pace accelerating at the acceleration rate of gravity.

Embodiments of the present invention may provide an apparatus including an imaging station with a plurality of image capture devices trained on an article receiving area configured to capture a plurality of images of an article passing through the article receiving area of the imaging station. Apparatuses may include a packaging station where a container is configured to receive an article passing through the imaging station, and an identification station configured to identify the article from at least one of the plurality of captured images and to generate information related to the identified article in response to identifying the article. Embodiments may include a labeling station configured to cause the information related to the identified article to be presented on a label associated with the container. The information related to the identified article may include destination information associated with a destination associated with the identified article. The identification station may be configured to identify the article from at least one of the plurality of captured images based on a barcode. The labeling station may provide for transmission of a signal including the information related to the identified article to an electronic display of the container. The labeling station may include a printer configured to print the information related to the identified article to a label associated with the container.

According to some embodiments, the labeling station may include a radio-frequency identification encoder configured to encode a radio frequency identification tag with the information related to the identified article. The packaging station may be configured to seal the container with a tamper-evident closure in response to receiving the article passing through the imaging station.

Embodiments of the present invention may provide a computer program product including at least one non-transitory computer-readable storage medium having computer-readable program instructions stored therein. The computer-readable program instructions may include program code instructions to cause a plurality of images of an article to be captured, and program code instructions to determine, from the plurality of images, an identification of the article. Embodiments may optionally include program code instructions to generate information related to the article, and program code instructions to cause the information related to the article to be displayed on a container that has received the article. Embodiments may include program code instructions to store at least one of the plurality of images, the identification of the article, and the information related to the article as a record. Embodiments may optionally include program code instructions to cause a record to be presented on a display for review, program code instructions to receive an approval in response to the identification of the article and the information related to the article being determined to be correct, and program code instructions to receive a rejection in response to the identification of the article and the information related to the article being determined to be incorrect.

BRIEF DESCRIPTION OF THE SEVERAL VIEWS OF THE DRAWINGS

Reference will now be made to the accompanying drawings, which are not necessarily drawn to scale, and wherein:

FIG. 7 is a flowchart of a method for identifying an article for repackaging and labeling of the article.

DETAILED DESCRIPTION

Figure 1:
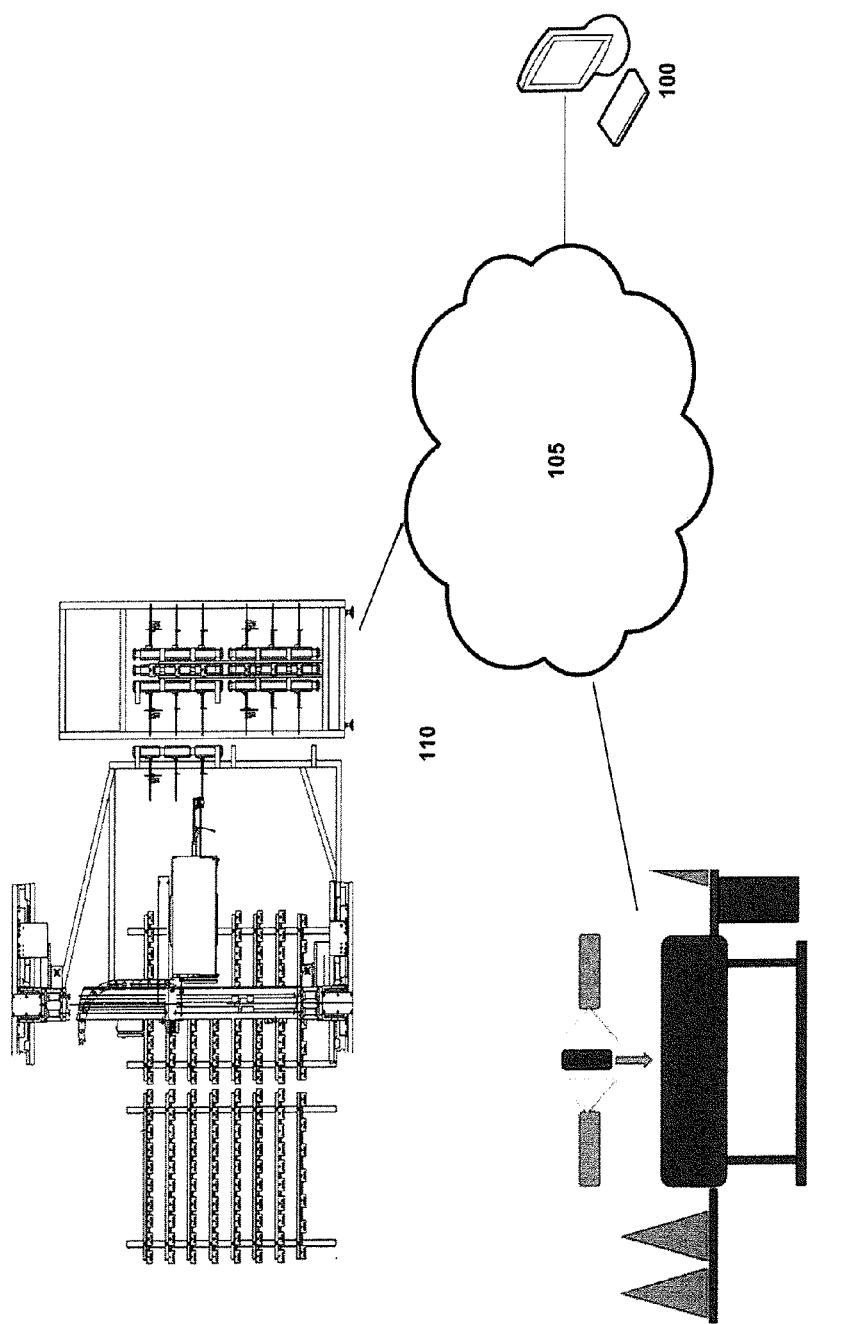
FIG. 1 illustrates a system that can be used in conjunction with various embodiments of the present invention.

Embodiments of the present invention now will be described more fully hereinafter with reference to the accompanying drawings, in which some, but not all embodiments of the invention are shown. Indeed, the invention may be embodied in many different forms and should not be construed as limited to the embodiments set forth herein; rather, these embodiments are provided so that this disclosure will satisfy applicable legal requirements. Like numbers refer to like elements throughout. The terms top, bottom, side, up, down, upwards, downwards, vertical, horizontal, and the like as used below do not imply a required limitation in all embodiments of the present invention but rather are used herein to help describe relative direction or orientation in exemplary embodiments illustrated in the figures.

As should be appreciated, various embodiments may be implemented in various ways, including as methods, apparatus, systems, or computer program products. Accordingly, various embodiments may take the form an embodiment in which a processor is programmed to perform certain steps. Furthermore, various implementations may take the form of a computer program product on a non-transitory computer-readable storage medium having computer-readable program instructions embodied in the storage medium. Any suitable computer-readable storage medium may be utilized including hard disks, CD-ROMs, optical storage devices, or magnetic storage devices.

Various embodiments are described below with reference to block diagrams and flowchart illustrations of methods, apparatus, systems, and computer program products. It should be understood that each block of the block diagrams and flowchart illustrations, respectively, may be implemented in part by computer program instructions, e.g., as logical steps or operations executing on a processor in a computing system. These computer program instructions may be loaded onto a computer, such as a special purpose computer or other programmable data processing apparatus to produce a specifically-configured machine, such that the instructions which execute on the computer or other programmable data processing apparatus implement the functions specified in the flowchart block or blocks.

These computer program instructions may also be stored in a computer-readable memory that can direct a computer or other programmable data processing apparatus to function in a particular manner, such that the instructions stored in the computer-readable memory produce an article of manufacture including computer-readable instructions for implementing the functionality specified in the flowchart block or blocks. The computer program instructions may also be loaded onto a computer or other programmable data processing apparatus to cause a series of operational steps to be performed on the computer or other programmable apparatus to produce a computer-implemented process such that the instructions that execute on the computer or other programmable apparatus provide operations for implementing the functions specified in the flowchart block or blocks.

Accordingly, blocks of the block diagrams and flowchart illustrations support various combinations for performing the specified functions, combinations of operations for performing the specified functions, and program instructions for performing the specified functions. It should also be understood that each block of the block diagrams and flowchart illustrations, and combinations of blocks in the block diagrams and flowchart illustrations, can be implemented by special purpose hardware-based computer systems that perform the specified functions or operations, or combinations of special purpose hardware and computer instructions.

FIG. 1 provides an illustration of a system that can be used in conjunction with various embodiments of the present invention. As shown in FIG. 1, an example embodiment of the system may include an automated dispensing system 110, one or more networks 105, and an automated repackaging station 120. Embodiments may include various other devices which may be in communication with the one or more networks 105, such as an approval station 100 which may be used for manual review and/or audit of an automated process performed by one or both of the automated dispensing system 110 and the automated repackaging station 120. Embodiments may further include other network entities from which data may be received from or transmitted to, as will be described further below. Each of the components of the system may be in electronic communication with, for example, one another over the same or different wireless or wired networks (e.g., network 105) including, for example, a wired or wireless Personal Area Network (PAN), Local Area Network (LAN), Metropolitan Area Network (MAN), Wide Area Network (WAN), or the like. Additionally, while FIG. 1 illustrates the various system entities as separate, standalone entities, the various embodiments are not limited to this particular architecture.

Figure 2:
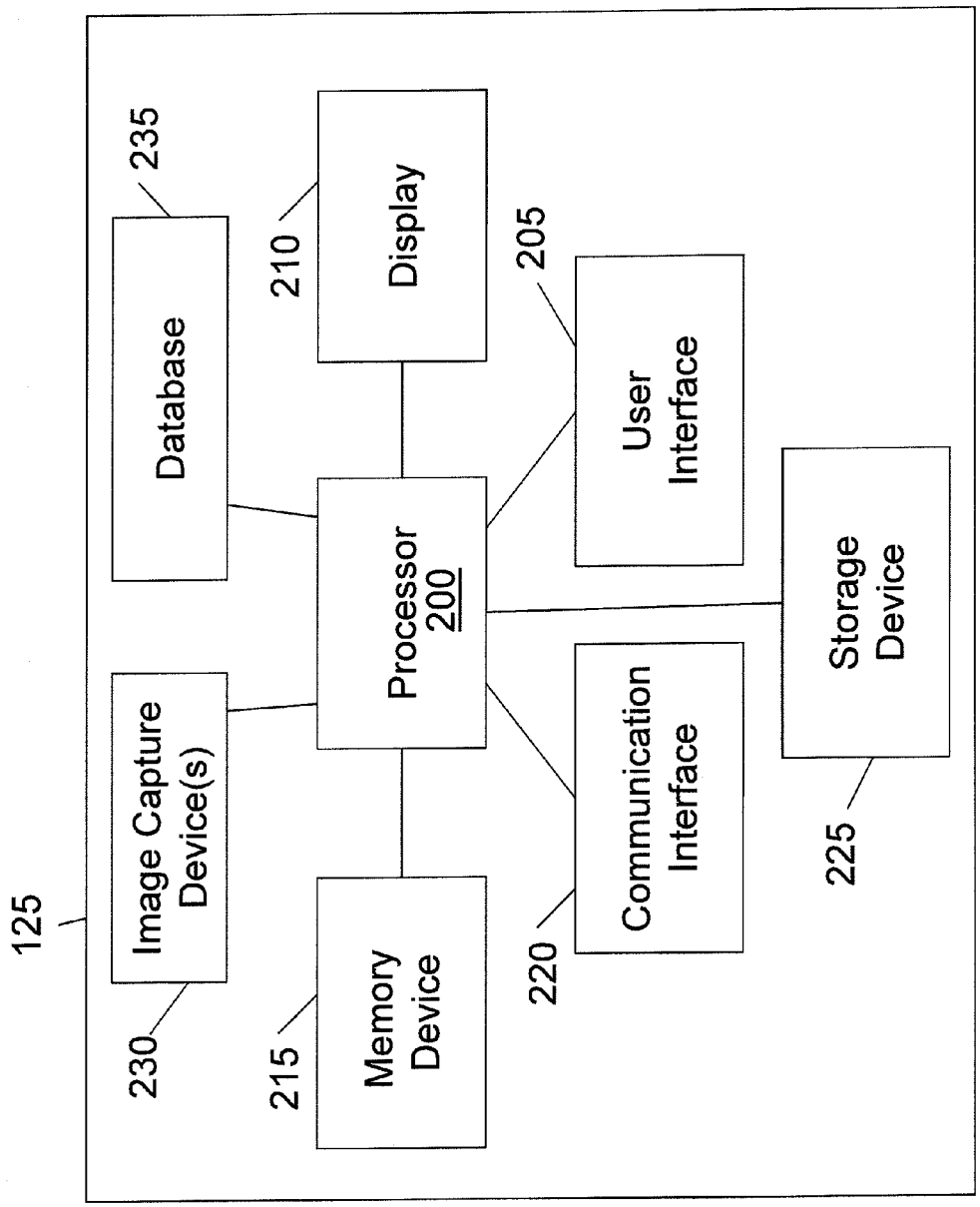
FIG. 2 illustrates a schematic diagram of an automated packaging station controller according to an example embodiment of the present invention.

Example embodiments of the automated repackaging station 120 as described herein may include a controller configured to control or otherwise monitor and facilitate activities performed at the automated repackaging station 120. FIG. 2 provides a schematic of an example embodiment of a controller 125 of an automated repackaging station 120. In general, the term "controller" may refer to, for example, any computer, computing device, mobile phone, desktop, tablet, notebook or laptop, distributed system, server, blade, gateway, switch, processing device, or combination of processing devices adapted to perform the functions described herein. The automated repackaging station controller 125 may include, be associated with, or be in communication with a variety of computing entities, such as pharmacy inventory management systems, a medication identification database, medication dispensing units, data storage/facilitation computing entities, or other devices that may interface with inventory management, dispensing, replenishing, etc. While example embodiments of automated dispensing systems may be implemented in virtually any setting which may benefit from automated dispensing of articles, embodiments described herein will be described generally with respect to the field of healthcare in which medications may be dispensed for patients or caregivers. However, it is appreciated that embodiments of the present invention may apply to various other embodiments of automated dispensing systems and devices.

Automated repackaging stations according to example embodiments of the present invention may be configured to repackage medications or articles that are already in a package, such as a unit dose package, a medication vial, or an intravenous bag, for example. In this manner, automated repackaging stations 120 as described herein may be configured to package medication into an overpack to hold the medication without removing the medication or supplies from their original packaging. Overpacks may be means for packaging medication into a package that is more conducive to automated handling, or more conducive to a particular method of storage. The overpacks may facilitate uniform handling to ease distribution and tracking within a healthcare facility.

Overpacks or packaging that encases or holds the medication or supplies may also be used in order to provide a more uniform form factor for medications and supplies to be handled and dispensed throughout a healthcare facility. Overpacks may provide a common size, profile, shape, or grasping feature. Various embodiments of overpacks may include uniform or quasi-uniform overpacks for use with a variety of medications and supplies with varying shapes, sizes, and handling requirements (e.g., fragile, temperature sensitive, etc.). The uniformity or quasi-uniformity of such overpacks may provide an aspect of uniformity to generally non-uniform form factors. The uniformity may be in the profile of the overpack, such as when the overpack includes a plurality of various sized bins with uniform profiles, or the uniformity may be in a locating/holding hole of a plurality of various sized bags configured to hold the various form factors.

As described above, an automated repackaging station 120 according to example embodiments may include a repackaging station controller, such as the illustrated embodiment of FIG. 2. The automated repackaging station controller 125 may include a processor 200 that communicates with other elements of the automated repackaging station controller 125 via a system interface or bus. The processor 200 may be embodied in a number of different ways. For example, the processor 200 may be embodied as a processing element, processing circuitry, a coprocessor, a controller or various other processing devices including integrated circuits such as, for example, an application specific integrated circuit (ASIC), a field programmable gate array (FPGA), a hardware accelerator, and/or the like.

In an example embodiment, the processor 200 may be configured to execute instructions stored in memory or otherwise accessible to the processor 200. As such, whether configured by hardware or software methods, or by a combination thereof, the processor 200 may represent an entity capable of performing operations according to embodiments of the present invention when configured accordingly. For example, as discussed in more detail below, the automated repackaging station controller 125 may be configured, among other things, to facilitate accurate identification of pre-packaged medication. The automated repackaging station controller 125 may also be used to generate and/or provide information related to an identified pre-packaged article for labeling of an overpack containing the pre-packaged article. A user interface 205 may be configured for user input to initiate the automated repackaging process or to confirm, advance, or otherwise interact with operations of the automated repackaging process. The user interface 205 may include a keyboard, a pointing device, or other mechanism for a user to communicate with the processor 200 and interact with the automated repackaging station controller 125.

Automated repackaging station controllers 125 according to example embodiments may further include a display 210 which may be configured to present information to a user pertaining to the automated repackaging process and to communicate alerts or confirm success of various steps of the automated repackaging process. The display 210 may also be configured to present information to a user pertaining to the status of the automated repackaging station, information regarding inventory, or any information which may be useful to a user of the device. The display 210 may include a touch screen display which may partially or fully comprise the user interface 205. As noted above, example embodiments may include an automated repackaging station that also incorporates the approval station. In such an embodiment, the user interface 205 and display 210 may be used for the approval of operations of the repackaging process, auditing the automated repackaging process, or reviewing rejected, unidentified unit dose medications as will be further detailed below.

The automated repackaging station controller 125 may further include or be in communication with one or more image capture devices 230. The image capture devices may include still cameras, video cameras, scanning devices, and/or the like. The image capture devices 230 of embodiments of the present invention may be used to capture images and/or video of a pre-packaged medication or article as it is received through an identification station about which the image capture devices are disposed. Embodiments of the controller may further include or be in communication with a database 235 which may be in communication with a healthcare facility network. The database may include information relating to the medication and supplies that may be identified by images captured through the image capture devices 230. The information may relate to a destination for an identified medication, an expiration date for a medication, a packaging date for a medication, etc. The database 235, as with any of the components of the automated packaging station controller 125, may be located remotely from the controller and may be accessed via a wired or wireless network. As such, the database may include identifying information for all of the medications and supplies configured to be repackaged by the automated repackaging station.

The automated repackaging station controller 125 may further include transitory and non-transitory memory device 215, which may include both random access memory (RAM) and read only memory (ROM). The ROM may be used to store a basic input/output system (BIOS) containing the basic routines that help to transfer information to the different elements within the automated repackaging station controller 125.

In addition, in one embodiment, the automated repackaging station controller 125 may include at least one storage device 225, such as a hard disk drive, a CD drive, and/or an optical disk drive for storing information on various computer-readable media. The storage device(s) 225 and its associated computer-readable media may provide non-volatile storage. The computer-readable media described above could be replaced by any other type of computer-readable media, such as embedded or removable multimedia memory cards (MMCs), secure digital (SD) memory cards, Memory Sticks, electrically erasable programmable read-only memory (EEPROM), flash memory, hard disk, and/or the like. The storage device may be configured to store, for example, an audit trail of medications or supplies repackaged, operations, errors, alerts, and manual identification of medications or supplies rejected by the identification system described below.

Furthermore, a number of executable instructions, applications, scripts, program modules, and/or the like may be stored by the various storage devices 225 and/or within memory device 215. As discussed in more detail below, these executable instructions, applications, program modules, and/or the like may control certain aspects of the operation of the automated repackaging station controller 125 with the assistance of the processor 200 and operating system, although their functionality need not be modularized. In addition to the program modules, the automated repackaging station controller 125 may store or be in communication with one or more databases.

Also located within the automated repackaging station controller 125, in one embodiment, is a communication interface 220 for interfacing with various computing entities. This communication may be via the same or different wired or wireless networks (or a combination of wired and wireless networks). For instance, the communication may be executed using a wired data transmission protocol, such as fiber distributed data interface (FDDI), digital subscriber line (DSL), Ethernet, asynchronous transfer mode (ATM), frame relay, data over cable service interface specification (DOCSIS), or any other wired transmission protocol. Similarly, the automated storage device controller 100 may be configured to communicate via wireless external communication networks using any of a variety of protocols, such as 802.11, general packet radio service (GPRS), Universal Mobile Telecommunications System (UMTS), Code Division Multiple Access 2000 (CDMA2000), CDMA2000 1× (1×RTT), Wideband Code Division Multiple Access (WCDMA), Time Division-Synchronous Code Division Multiple Access (TD-SCDMA), Long Term Evolution (LTE), Evolved Universal Terrestrial Radio Access Network (E-UTRAN), Evolution-Data Optimized (EVDO), High Speed Packet Access (HSPA), High-Speed Downlink Packet Access (HSDPA), IEEE 802.11 (Wi-Fi), 802.16 (WiMAX), ultra wideband (UWB), infrared (IR) protocols, Bluetooth™ protocols, wireless universal serial bus (USB) protocols, and/or any other wireless protocol.

It will be appreciated that one or more of the automated repackaging station controller's 125 components may be located remotely from other automated repackaging station controller components. For example the storage device 225 may be located on a remote network entity. Furthermore, one or more of the components may be combined and additional components performing functions described herein may be included in the automated repackaging station controller 125.

Figure 3:
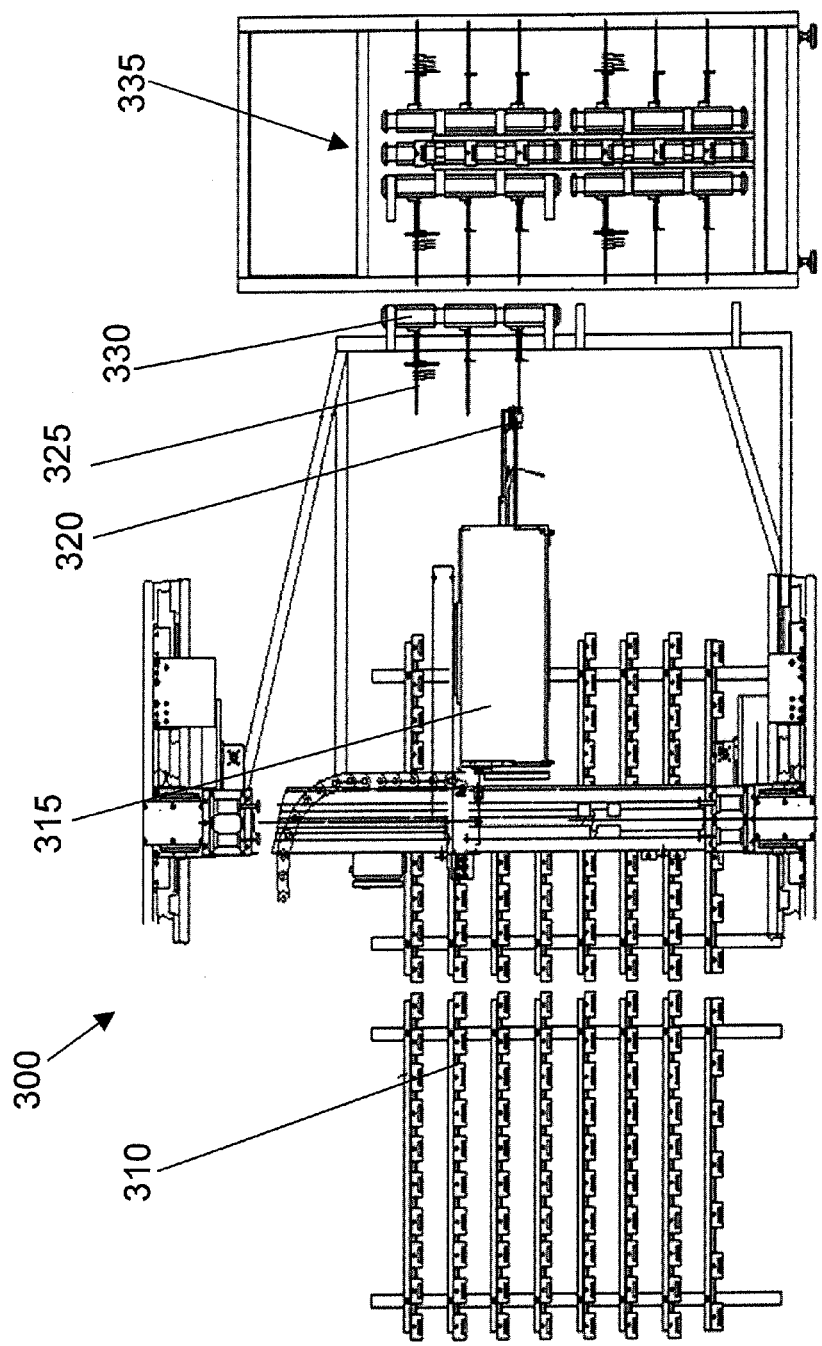
FIG. 3 illustrates an example embodiment of an automated dispensing system which may benefit from example embodiments of the present invention.

In one embodiment, an automated dispensing system may be used to hold/store/dispense various medications. Such dispensing systems may be used in a variety of environments, including retail pharmacies, central fill pharmacies, hospitals, etc. FIG. 3 illustrates an example embodiment of an automated dispensing system 300 which may be configured to automatically dispense individual unit dose packages of medication in response to receiving a prescription order. Automated dispensing systems 300 which may benefit from example embodiments of the present invention may include a storage rack 310 which stores medication, such as unit dose packages, a robotic system 315 for retrieving the stored medications, where the robotic system 315 includes an end-of-arm-tool for moving the medications, and a dispensing area 335 where medications are dispensed for retrieval by a nurse, doctor, pharmacy technician, etc. In some embodiments, the dispensing system 300 may include bulk transfer devices, such as the portable carrier 330 which is configured to hold multiple medications for faster transfer between the storage rack 310 and the dispensing area 335.

Figure 4:
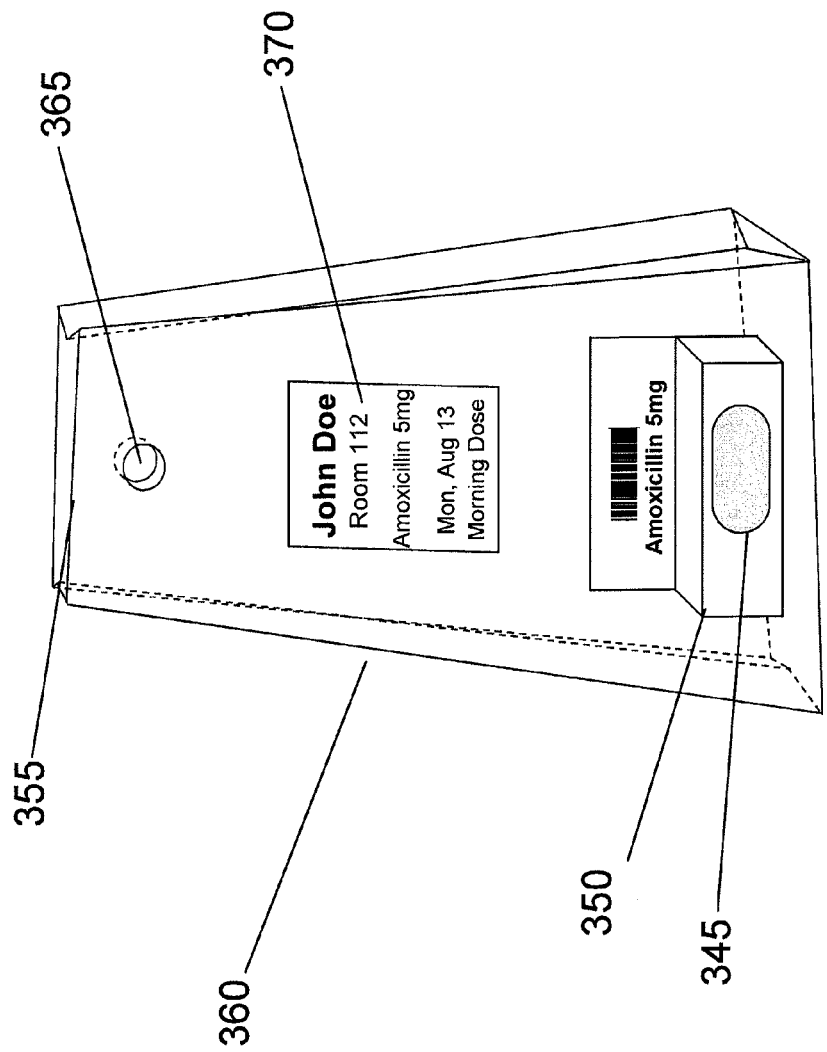
FIG. 4 illustrates an example embodiment of a unit dose of medication in an overpack package which may be used in conjunction with example embodiments of the present invention.

Automated dispensing systems as described above and illustrated in FIG. 3 may require specific packaging that is compatible with the robotic system 315 and the end-of-arm-tool 320. An illustration of an example embodiment of such packaging is illustrated in FIG. 4 which depicts a blister-pack type package 350. The blister-pack 350 carries the medication 345. According to the illustrated embodiment, the blister-pack type package 350 is received within a bag-type overpack 360. The overpack 360 may include a feature that is conducive to automated handling. In the illustrated embodiment, the overpack 360 includes holes 365 configured to be engaged by a rod for storage and for dispensing using a system such as dispensing system 300 of FIG. 3. The overpack 360 may further include a feature, such as a tamper-evident closure proximate the top 355 of the bag. The tamper-evident feature may include an adhesive seal or other type of closure which provides a visual indication once the seal has been compromised.

According to some embodiments of the present invention, overpacks 360 may include a label 370 that includes information about the medication contained within the overpack, but the label may also include information related to the medication, such as a person for whom the medication is intended, a location of the person, a date for dispensing (and/or of packaging), an indication of the time of day that the medication is to be administered, or any other information relating to the article within the overpack 360.

Further, while the illustrated dispensing system of FIG. 3 and the medication packaging of FIG. 4 are configured to be stored on rod-type storage systems, various other forms of storage may be implemented in further embodiments of the present invention using various styles of overpacks. For example shelf-based storage on which boxes or structured packaging for medication is held for retrieval by a robotic system or clamp-based storage in which various types of packaging may be clipped for storage and retrieval by a robotic system, among others. As such, the type of packaging illustrated herein and the type of automated dispensing system are merely examples and should not be construed as limiting.

Figure 5:
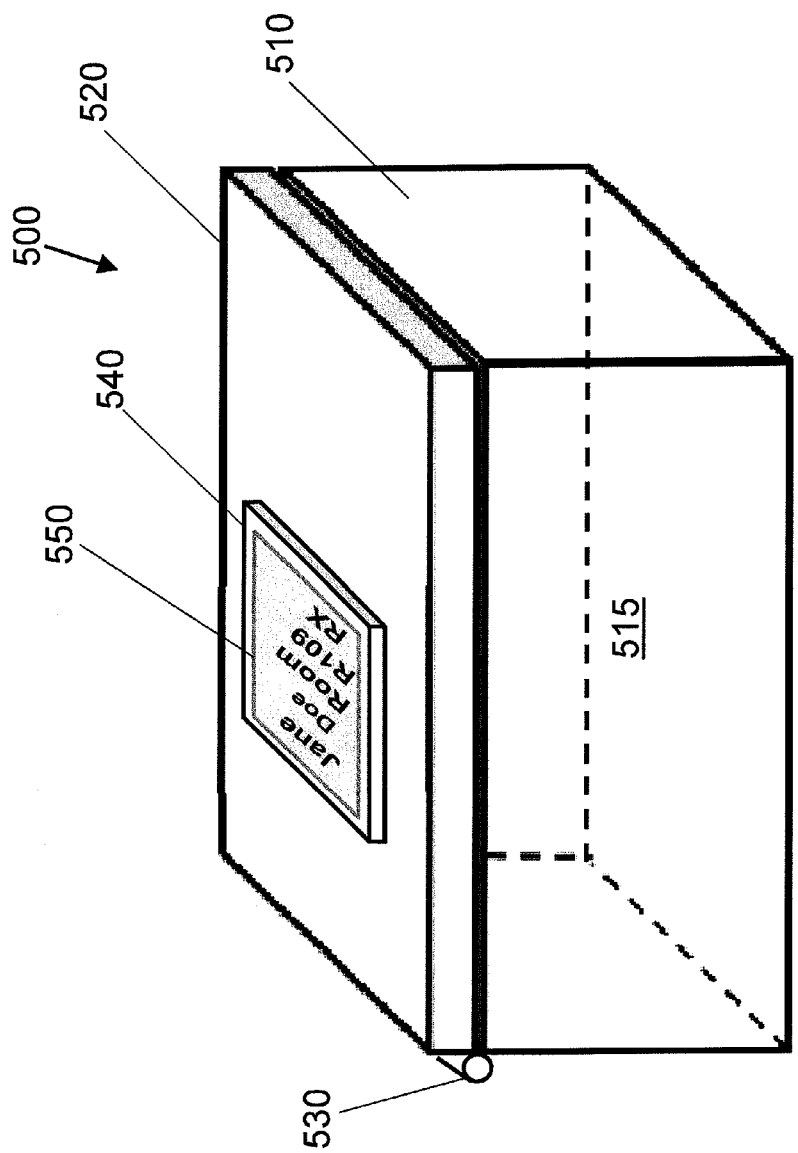
FIG. 5 illustrates another example embodiment of an overpack package which may be used in conjunction with example embodiments of the present invention.

FIG. 5 illustrates another type of overpack which may be implemented according to embodiments of the present invention. The illustrated embodiment depicts a bin 500 that has a base 510 including a cavity for receiving an article therein, and a lid 520. The lid 520, which may not be present in some embodiments, may be hinged proximate an edge of the lid, such as at hinge 530. The bin 500 may also include a label 540 with a digital display 550, such as an electronic-ink display. The bin 500 of the illustrated embodiment may receive an article therein with the lid in an open position and the lid may be closed to seal the contents. The bin 500 may include a tamper evident seal, or may have a tamper evident seal affixed thereto in response to the bin receiving the article and the lid 520 being closed. Optionally, the lid may include a locking feature which may be locked in response to the lid being closed. Such a lock may be similar to that of a retail keeper, popular in the retail industry for theft deterrence of high-value goods (requiring a managers/nurses key to be opened), or the lock may be electronically actuated by a locking mechanism disposed in the lid 520 or attached to the base 510.

As outlined above, automated dispensing systems are generally implemented in environments where large quantities of medications are dispensed routinely, such as hospitals, central fill pharmacies serving several hospitals, healthcare facilities, and the like. As such, automated dispensing systems may dispense thousands to hundreds of thousands of individual unit doses annually. Thus, automated repackaging stations may repackage as many articles on an annual basis.

In order to ensure proper handling and dispensing of these medications, repackaged medications must be provided with appropriate labeling which may include an identifying barcode (one-dimension or two-dimension), a name, an encoded radio frequency identification (RFID) chip, or other identifying indicia. It is imperative that the medication contained within the original packaging match the identifying information contained on the overpack packaging. As automated dispensing systems and other devices, such as bed-side scanners used by nurses, may rely on the identification on the overpack, the identifying information must be correct. Further, as a nurse, doctor, or patient may not know what the medication should look like, and because many medications resemble one another, it is important to properly identify the medication overpack to avoid a patient receiving the incorrect medication (either type or dose).

Embodiments of the present invention provide a method, apparatus, and computer program product to identify an article, such as a medication or supply, such that it can be properly labeled in an overpack when the article is repackaged. The accurate labeling of the overpack improves the efficiency and accuracy of handling and transportation throughout a healthcare facility.

Figure 6:
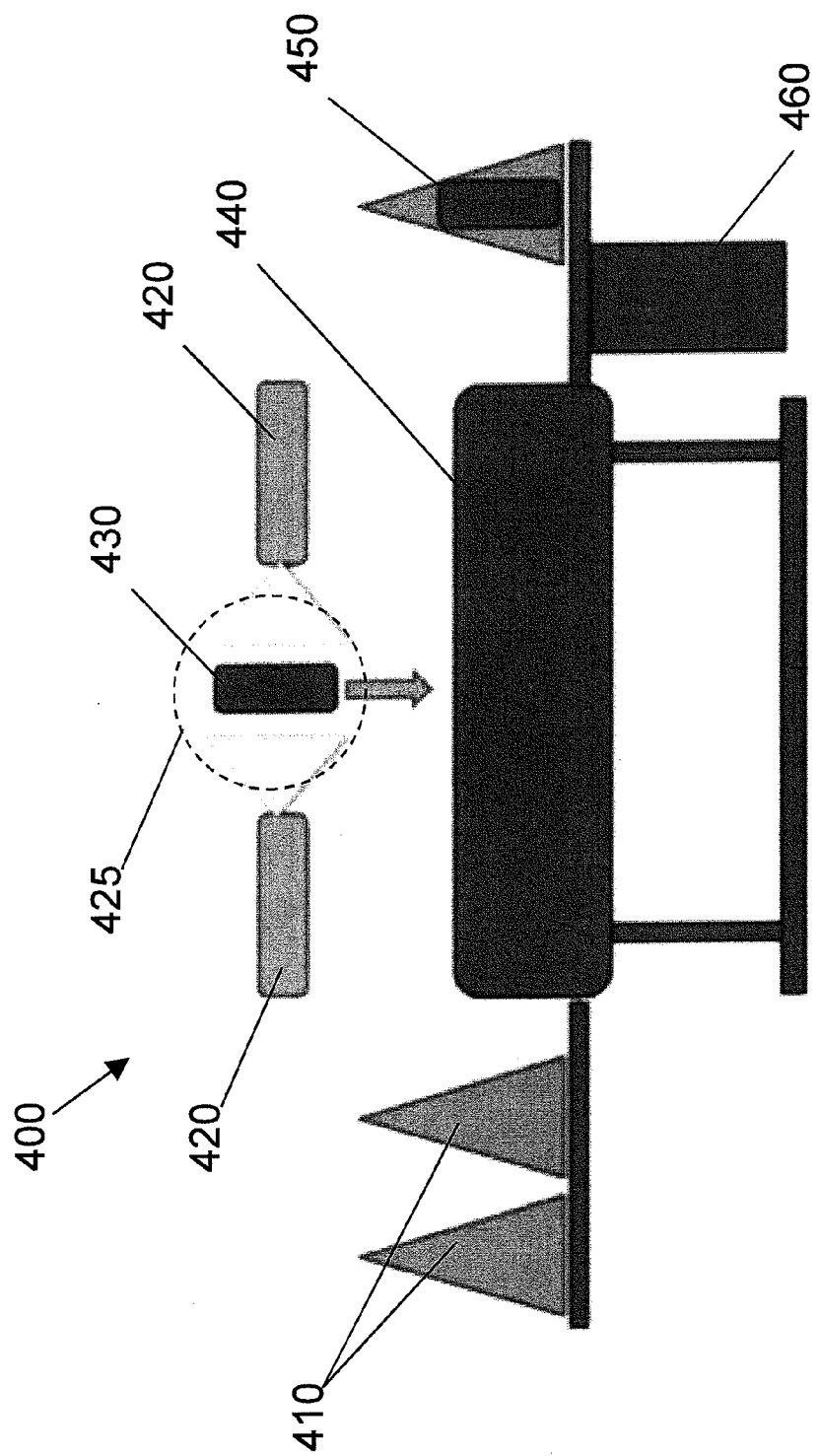
FIG. 6 is an illustration of an automated repackaging station according to an example embodiment of the present invention.

FIG. 6 illustrates an example embodiment of an identification system implemented in an automated repackaging station 400 in accordance with the present invention. In the illustrated embodiment, empty overpacks 410 may be received at the automated repackaging station 400. The empty overpacks 410 may be received in an automated manner, such as along a conveyor, into the repackaging machine 440. Articles, such as article 430, may be dispensed from a hopper or conveyor located above the repackaging machine 440. The articles may move through, or be dropped through an imaging station which may include a plurality of image capture devices 420 disposed about an article receiving area 425. As the article 430 moves through the article receiving area 425, the image capture devices 420 capture a plurality of images of the article 430. While the illustrated embodiment depicts a repackaging machine configured to receive articles dropped through the imaging station, moving at a constant rate of acceleration (i.e., gravity), alternative methods of moving the article through the imaging station may be employed. For example, the imaging station may be fed via a conveyor (e.g., a constant velocity conveyor) or a feed-stop conveyor arranged to vary the speed of the conveyor according to the needs of the imaging station.

The image capture station or imaging station may include a plurality of image capture devices trained on an article receiving area that are configured to capture a plurality of images of an article passing through the article receiving area, such as by gravity or by a conveyor. While the imaging station may be configured to capture a variety of images from a variety of angles about an article in the article receiving area, according to some embodiments, the imaging station may include multiple discrete areas or positions within the imaging station. For example, the imaging station may include a first area where one or more image capture devices capture images of an article from one or more first angles, and the imaging station may include a second area where one or more image capture devices capture images of an article from one or more second angles. In this manner, all angles of the article may be captured through a sequence of imaging areas of the imaging station. Further, each area may include a different color background to provide improved contrast between an article and the background for more effective imaging of the article. For example, a first background may be red, while a second background may be black, enabling different colored printing, media, or images may be more apparent with one background color than they are with a second background color. The article receiving area may be a single position along the path of travel of an article, if all image capture devices are trained on the same area, or the receiving area may be the path through the imaging station along which images are captured if the images are not captured all at one location.

As described above, the image capture devices are in communication with an automated repackaging controller 125. The images of the article 430 may be transmitted to a processor (e.g., processor 200) or to a remote system for proper identification. The image capture device 420 may communicate with a processor or remote system via a wired or wireless connection, such as by connection with a network. The captured images of the article 430 may be analyzed by the controller (e.g., by processor 200) to determine an identification of the article 430. The article may include, for example, a barcode or other identifying indicia configured to be interpreted by the controller 125. Upon identifying the article 430, the controller 125 may generate information relating to the identified article.

In an example embodiment in which the article is not properly identified, the automated repackaging station 400 may provide an alert to an operator that the article wasn't properly identified such that the article may be manually identified or reprocessed by the station. In some example embodiments, an article that is not properly identified may be re-routed by the repackaging station 400 to be re-processed by the repackaging station in an effort to minimize the need for human interaction.

When an article is properly identified, according to some embodiments of the present invention, the controller 125 may be in communication with a network of a healthcare facility and may be configured to generate information based on the identification of the article 430, and information related to patients of the healthcare facility, such as prescription orders. Thus, the controller 125 may be configured to generate information about the article 430 which may relate to the patient for whom the article or medication is intended, a room or location where the patient is located, a day and/or time that the medication is to be administered, or other relevant information about the article. Further, the information about the article 430 may include an expiration date of the article, handing instructions (e.g., if refrigeration required), an administration instruction, etc. While some of this information may be read from the article 430 itself, other information may be obtained through prescription orders, a database of medication handling instructions, a database of patient locations in a healthcare facility, etc. The automated generation of information related to the article 430 received into the container may improve the accuracy of labeling of overpacks and may reduce or eliminate the need for manual verification of each medication and overpack label.

The information that is generated relating to the identified article may be provided for presentation on the overpack of the article. Some or all of the information may be printed to a label that is affixed to the overpack, such as by printer 460. Optionally, the overpack may include a label disposed thereon such that the information is printed or written directly to the overpack. In some example embodiments, the overpack may include a thermal transfer label portion to which a thermal transfer printer writes the generated information. In some embodiments, the generated information may be encoded to a radio frequency identification tag that may be attached to the overpack. The radio frequency identification tag may be written to by a radio frequency identification encoder. While this information may not be in a human-readable format, the radio frequency identification tag of the overpack may be scanned by a reader to convert the stored information to a human-readable format. Further, radio frequency tags may be used to track the location of the overpacks throughout a healthcare facility. In other example embodiments, the overpack may include an electronic label, such as an electronic ink label which may be written to and re-written by an encoding device of the repackaging station 400.

The overpack containing the article 430 may be sealed with a tamper-evident seal, as described above, to discourage unauthorized access or tampering with packaged medications. The tamper-evident seal may be an adhesive seal that seals the overpack closed as soon as an article is received therein, or before the overpack leaves the packaging machine 440 such that operator tampering with overpack contents is precluded. Once the overpack 430 has been properly labeled with the generated information and the overpack is sealed, a repackaged product 450 may be ready for dispensing in the healthcare facility.

The images captured by the image capture devices 420, the generated information that is to be presented on the overpack, and additional information, such as the date and time of the repackaging of the article may be stored as a record, such as in memory device 215 of the controller 125. The record may include all of the information needed by a pharmacist to check or audit the accuracy of repackaging. Random sampling may be conducted by a pharmacist or authorized healthcare personnel to confirm the accuracy of the repackaging station 400. Records of repackaging operation may be provided at the desired interval or rate in order to ensure consistency and accuracy in the repackaging of medications.

While the above described mechanisms for identifying an article describe positively identifying an article by establishing a match between the dispensed article and a known article, determining a "match" between the captured images and known articles may be based on a confidence level. For example, as each captured image for each unit dose of medication may vary to some degree, exact article matches for the captured image may not be found. Therefore, to improve the rate at which articles are identified, known articles in the database that match a captured image of a unit dose of medication above a threshold level may be considered a "match."

In an example embodiment of establishing a match, a captured image of an article may include an article that is identified using a partial barcode and a portion of the label. Embodiments of the repacking controller may be configured to match the partial barcode and portions of the label with a known medication within a predetermined confidence level, wherein the medication is considered positively identified.

The predetermined confidence level which must be satisfied to establish a match between a unit dose of medication in a captured image and the database of known medications may be variable and may be calibrated in order to achieve a minimum accuracy rate (e.g., 99.9999%). The threshold may also vary depending upon the characteristics of the medication or original packaging. For example, many medications are packaged in unit-dose blisters. As such, when a unit dose blister is in the captured image, the confidence threshold that must be satisfied may be substantially higher than if the article is a small vial of a brightly colored fluid, where the system only includes one article type that corresponds to those characteristics.

FIG. 7 illustrates an example embodiment of a method for identifying articles in a packaging system. An article may be received at an imaging station as shown at 500. Images of the article may be captured from a plurality of positions about the imaging station at 510. The article may be identified from at least one of the captured images as shown at 520. Information related to the identified article may be generated in response to identifying the article at 530. Information related to the identified article may be caused to be presented on a label associated with the container at 540.

In an example embodiment, an apparatus for performing the method of FIG. 7 above may include a processor (e.g., the processor 200) configured to perform some or each of the operations (500-540) described above. The processor 200 may, for example, be configured to perform the operations (500-540) by performing hardware implemented logical functions, executing stored instructions, or executing algorithms for performing each of the operations. Alternatively, the apparatus may comprise means for performing each of the operations described above. In this regard, according to an example embodiment, examples of means for performing operations 500-540 may comprise, for example, the repackaging station controller 125 (or respective different components thereof). Additionally or alternatively, at least by virtue of the fact that the processor 200 may be configured to control or even be embodied as the repackaging station controller 125, the processor 200 and/or a device or circuitry for executing instructions or executing an algorithm for processing information as described above may also form example means for performing operations 500-540.

Many modifications and other embodiments of the inventions set forth herein will come to mind to one skilled in the art to which these inventions pertain having the benefit of the teachings presented in the foregoing descriptions and the associated drawings. Therefore, it is to be understood that the inventions are not to be limited to the specific embodiments disclosed and that modifications and other embodiments are intended to be included within the scope of the appended claims. Moreover, although the foregoing descriptions and the associated drawings describe some example embodiments in the context of certain example combinations of elements and/or functions, it should be appreciated that different combinations of elements and/or functions may be provided by alternative embodiments without departing from the scope of the appended claims. In this regard, for example, different combinations of elements and/or functions than those explicitly described above are also contemplated as That which is claimed:

1. A method comprising:
receiving an article at an imaging station;
capturing images of the article from a plurality of positions about the imaging station;
identifying the article from at least one of the captured images, wherein the at least one of the captured images comprises identifying indicia;
generating information related to the identified article in response to identifying the article; and
causing the information related to the identified article to be presented on a label associated with a container into which the article is received.

2. The method of claim 1, wherein generating information related to the identified article comprises generating destination information associated with the article.

3. The method of claim 1, wherein the identifying indicia comprises a barcode.

4. The method of claim 1, wherein the container comprises a bin, and wherein causing information related to the identified article to be presented on a label associated with the container comprises causing an electronic display to present the information related to the identified article.

5. The method of claim 1, further comprising generating and storing to a memory a record comprising the at least one of the captured images and the information related to the identified article.

6. The method of claim 5, further comprising providing for presentation of the record to a user; and receiving verification that the at least one of the captured images and the information related to the identified article are correct.

7. The method of claim 1, wherein the imaging station comprises a plurality of image capture devices disposed about a receiving area, and wherein receiving an article at the imaging station comprises receiving an article through the receiving area at an uninterrupted pace.

8. The method of claim 7, wherein capturing images of the article from a plurality of positions about the imaging station comprises capturing images of the article as the article moves through the receiving area at an uninterrupted pace.

9. The method of claim 8, wherein the uninterrupted pace is a pace accelerating at the acceleration rate of gravity.

10. An apparatus comprising:
an imaging station comprising a plurality of image capture devices trained on an article receiving area configured to capture a plurality of images of an article passing through the article receiving area of the imaging station;
a packaging station wherein a container is configured to receive an article passing through the imaging station;
an identification station configured to identify the article from at least one of the plurality of captured images and to generate information related to the identified article in response to identifying the article; and
a labeling station configured to cause the information related to the identified article to be presented on a label associated with the container.

11. The apparatus of claim 10, wherein the information related to the identified article comprises destination information associated with a destination associated with the identified article.

12. The apparatus of claim 11, wherein the identification station is configured to identify the article from at least one of the plurality of captured images based on a barcode.

13. The apparatus of claim 10, wherein the labeling station provides for transmission of a signal including the information related to the identified article to an electronic display of the container.

14. The apparatus of claim 10, wherein the labeling station comprises a printer configured to print the information related to the identified article to a label associated with the container.

15. The apparatus of claim 10, wherein the labeling station comprises a radio-frequency identification encoder configured to encode a radio frequency identification tag with the information related to the identified article.

16. The apparatus of claim 10, wherein the packaging station is configured to seal the container with a tamper-evident closure in response to receiving the article passing through the imaging station.

17. A computer program product comprising at least one non-transitory computer-readable medium having computer-readable program instructions stored therein, the computer-readable program instructions comprising:
program code instructions to cause a plurality of images of an article to be captured;
program code instructions to determine, from the plurality of images, an identification of the article;
program code instructions to generate information related to the article; and
program code instructions to cause the information related to the article to be presented on at least one of a label or a display associated with a container that has received the article.

18. The computer program product of claim 17, further comprising program code instructions to store at least one of the plurality of images, the identification of the article, and the information related to the article as a record.

19. The computer program product of claim 18, further comprising:
program code instructions to cause a record to be presented on a display for review;
program code instructions to receive an approval in response to the identification of the article and the information related to the article being determined to be correct; and
program code instructions to receive a rejection in response to the identification of the article and the information related to the article being determined to be incorrect.

* * * * *